United States Patent
Hollis et al.

(10) Patent No.: US 9,029,804 B2
(45) Date of Patent: May 12, 2015

(54) AIR-STABLE, BLUE LIGHT EMITTING CHEMICAL COMPOUNDS

(75) Inventors: Thedford Keith Hollis, Oxford, MS (US); Xiaofei Zhang, Oxford, MS (US)

(73) Assignee: University of Mississippi, University, MS (US)

( * ) Notice: Subject to any disclaimer, the term of this patent is extended or adjusted under 35 U.S.C. 154(b) by 230 days.

(21) Appl. No.: 13/502,330

(22) PCT Filed: Oct. 19, 2010

(86) PCT No.: PCT/US2010/053273
§ 371 (c)(1),
(2), (4) Date: Apr. 16, 2012

(87) PCT Pub. No.: WO2011/050003
PCT Pub. Date: Apr. 28, 2011

(65) Prior Publication Data
US 2012/0205554 A1   Aug. 16, 2012

Related U.S. Application Data

(60) Provisional application No. 61/253,030, filed on Oct. 19, 2009, provisional application No. 61/253,424, filed on Oct. 20, 2009.

(51) Int. Cl.
| | |
|---|---|
| C09K 11/06 | (2006.01) |
| H01L 51/00 | (2006.01) |
| H05B 33/10 | (2006.01) |
| H05B 33/14 | (2006.01) |
| H01L 51/50 | (2006.01) |

(52) U.S. Cl.
CPC ............ H01L 51/0084 (2013.01); C09K 11/06 (2013.01); *C09K 2211/1007* (2013.01); *C09K 2211/1044* (2013.01); *C09K 2211/183* (2013.01); *C09K 2211/185* (2013.01); H01L 51/0083 (2013.01); H01L 51/0087 (2013.01); *H01L 51/5016* (2013.01); *H01L 51/5036* (2013.01); H05B 33/10 (2013.01); H05B 33/14 (2013.01); *Y02E 10/549* (2013.01)

(58) Field of Classification Search
None
See application file for complete search history.

(56) References Cited

U.S. PATENT DOCUMENTS

2008/0018221 A1 *   1/2008   Egen et al. ............... 313/483

* cited by examiner

*Primary Examiner* — Kamal Saeed
(74) *Attorney, Agent, or Firm* — Butler Snow LLP (57) ABSTRACT

We report the synthesis and characterization of four novel CCC-NHC pincer platinum(II) and palladium(II) complexes, which adopt a distorted square planar configuration. These complexes emit bright blue light in the solid state under UV irradiation with emissions that are stable in ambient atmosphere ($O_2$ and $H_2O$) for extended periods. We also report the synthesis and characterization of CCC-NHC pincer ligand nickel complexes, and solid state fluorescence spectra have been collected for two of the complexes reported. X-ray structural analysis of a representative compound exhibits a distorted square planar geometry. Finally, we report the synthesis and characterization of CCC-NHC pincer ligand complexes for abnormal carbenes, triazole, and BIA.

34 Claims, 6 Drawing Sheets

AIR-STABLE, BLUE LIGHT EMITTING CHEMICAL COMPOUNDS

CROSS-REFERENCES TO RELATED APPLICATIONS

This application claims the benefit of U.S. Provisional Application Nos. 61/253,030 filed Oct. 19, 2009 and 61/253,424 filed Oct. 20, 2009. Each application(s) is incorporated herein by reference in entirety.

STATEMENT REGARDING FEDERALLY SPONSORED RESEARCH OR DEVELOPMENT

This application was funded by a grant from the National Science Foundation (Grant number CHE0809732). The government has certain rights in this invention.

FIELD OF THE INVENTION

The present invention is generally directed toward light-emitting compounds and the methods of making them.

BACKGROUND OF THE INVENTION

Light emitters are the key element in Organic Light Emitting Diodes (OLEDs) and photovoltaic cells. By far most of these devices are fabricated and perform under an inert atmosphere to keep their essential components from decomposing. However, these are expensive fabrication conditions, and are difficult to work in. There exists a need for light emitters that are stable at less stringent requirements. Additionally, Current light emitting devices have a limited range for the color blue, therefore there is significant need for new examples that broaden the range and increase the lifetime of devices.

The development of new molecular architectures to impart desired physical and chemical properties is an area of much activity. Numerous groups have developed examples of N-heterocyclic carbene ligands (NHCs) and their derivatives,[1] originally reported by Arduengo,[2] which are widely applied in catalysis[3] and other areas.[4] Pincer ligands are one of the most widely researched and applied architectures in modern organometallic chemistry.[5] The confluence of NHCs and pincer ligand chemistry has seen much activity in recent years.[6] The aryl-bridged bis(NHC)-pincer ligands are of two major classes depending on the atoms making the bonds to the metal: CCC-NHC pincer complexes (xylylenyl-bridged,[7] phenylenyl-bridged systems[8]) and CNC-NHC pincer complexes (pyridylenyl-bridged,[9] 2,6-lutidenyl-bridged[10]). We have developed and disclose herein a unique class of CCC-bis(NHC) pincer ligand systems[8] that emit light and remain stable in air and water.

SUMMARY OF THE INVENTION

Air & water stable emitters will allow inexpensive fabrication conditions, more diverse working environments with anticipated longer lifetimes for the devices, i.e., a greater "value to cost" ratio is achievable.

We disclose herein a unique ligand architecture to manipulate the excited state of organometallic light emitters. Four blue light emitters have been recently synthesized and their composition and structure have been identified. Exposing the emitters to air and UV irradiation gave stable blue light emission for greater than one hour.

We further disclose herein the development and characterization of a new class of square planar CCC-NHC pincer complexes of metal and metalloids and their light absorbing and emitting properties. Specifically, we claim a compound having the formula:

wherein R is a an alkyl or aryl group or hydrogen, $R^1$ is an alkyl, aryl, hydrogen or heteroatom substituent, $R^2$, $R^3$, $R^4$, $R^5$ are selected from the group consisting of alkyls, aryls, hydrogen and heteroatom substituents, including Silicon, wherein M is selected from the group consisting of metals and metalloids, wherein L is a ligand, and x is any number between 0 and 3, and n is any number between 0 and 6.

We also disclose the extension of the metallation/transmetallation methodology to the synthesis and structural characterization of complexes of the group 10 metal, Ni, Pd, Pt, their solid state fluorescence spectra, and their unique ligand exchange properties. Finally, we have also disclosed the synthesis of 1,8-Anthracene Bridged Bis-NHC Pincer Complexes, the bis-triazole-carbene-based phenylene-bridged CCC-NHC pincer complexes, and the bis-abnormal-carbene-based phenylene-bridged CCC-NHC pincer complexes.

BRIEF DESCRIPTION OF THE DRAWINGS

Further advantages of the invention will become apparent by reference to the detailed description of preferred embodiments when considered in conjunction with the drawings.

DETAILED DESCRIPTION

The following detailed description is presented to enable any person skilled in the art to make and use the invention. For purposes of explanation, specific details are set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the scope of the invention. The present invention is not intended to be limited to the embodiments shown, but is to be accorded the widest possible scope consistent with the principles and features disclosed herein.

We disclose herein compounds that having the formula wherein R is an alkyl or aryl group that may contain heteroatoms, $R^1$ is a hydrogen, alkyl or aryl group that may contain heteroatoms substituent, $R^2$, $R^3$, $R^4$, $R^5$ are selected from the group consisting of hydrogen, alkyl or aryl groups that may contain heteroatoms, including silicon, wherein M is selected from the group consisting of metals and metalloids, wherein L is a ligand, and x is any number between 0 and 3, and n is any number between 0 and 6.

We disclose detailed methods for making these compounds and present several examples of the working process, including where M is platinum, palladium, and nickel. Furthermore we show that the light emitted from these ligand architectures have unique properties, such as the ability to emit true-blue light when stimulated either by visible or non-visible light, and the ability to remain stable in air or water, even under photostimulation. These complexes are therefore very useful in electroluminescent and photoluminescent applications such as OLED and plasma flat screens, the development of blue violet lasers, or other color lasers. Because they interact and harness UV light, they can be used in photovoltaic cells where they would function to capture part of the spectrum of solar energy and transfer that to another part of the cell. We have even used these compounds in a thin film, and on the surface of glass and ITO coated glass.

The CCC-NHC pincer ligand precursor was synthesized using a modified procedure according to the literature.[8,17] Spontaneous activation of the three C—H bonds of the tridentate ligand was achieved through the basicity and electrophilicity of $Zr(NMe_2)_4$.[8,18] Pd(II) or Pt(II) sources were added to the in situ prepared Zr reagent to achieve transmetallation (Scheme 1).

All reactions were carried out at room temperature under an inert atmosphere. The crude products were obtained as light yellow or white solids with good yields (40%-57%). The identity of the complexes was established by $^1H$ and $^{13}C$ NMR spectroscopy, ESI-MS, and elemental analysis. The carbene chemical shift of complexes 1 ($\delta$=177.5 ppm) and 2 ($\delta$=174.8 ppm) are in the usual range. The $^{13}C$ NMR data of 3 and 4 indicate very characteristic $^{195}Pt-^{13}C$ (NHC and aryl) couplings.[19] The NHC carbon signal of 3 was observed at 171.7 ppm with $^1J_{Pt-C}$=1168 Hz and the aryl carbon signal was observed at 133.8 ppm with $^1J_{Pt-C}$=937 Hz. The NHC carbon signal of 4 was observed at 170.5 ppm with $^1J_{Pt-C}$=1166 Hz and the aryl carbon signal was observed at 134.0 ppm with $^1J_{Pt-C}$=953 Hz).

Scheme 1. Synthesis of $CCC^{Bu}$-NHC-M(II)-X complexes 1-4.

1: M = Pd; X = Cl    2: M = Pd; X = Br
3: M = Pt; X = Cl    4: M = Pt; X = Br $MX_2L_2 = PdCl_2(PhCN)_2$, $PdBr_2(PhCN)_2$, $PtCl_2(COD)$, or $PtBr_2(COD)$

General Procedures: The CCC-pincer N-heterocyclic carbene ligand precursor was synthesized using a modified procedure according to the literature.[1,2] All starting materials were purchased from Sigma-Aldrich, Fisher or Strem. The reagents were used as received unless otherwise mentioned. All solvents used in reactions were dried and degassed by passage through a basic alumina column under Ar protection. All reactions involving organometallic reagents were carried out under a $N_2$ or Ar atmosphere using standard glovebox and schlenk line techniques. Nuclear magnetic resonance spectra were collected using Bruker Avance 300 and Bruker Avance 500 instruments. Chemical shifts are expressed in parts per million downfield from the standard, followed by the number of protons, splitting pattern and coupling constant (if applicable). Electro spray ionization-mass spectra were collected using a Waters Micromass ZQ mass spectrometer. Elemental analysis was carried out by Columbia Analysis Service. UV-visible absorption spectra were collected using a HP 8453 UV-Visible system. Emission spectra were collected using a PerkinElmer LS 55 fluorescence spectrometer. Photo-stability studies were carried out by exposing the solid sample to a certain wavelength radiation in open air. The light source for these studies was a Xenon bulb, and the detector was a CCD camera placed behind a filter next to the sample chamber.

Detailed Examples of the Embodiments

Complex 1: Synthesis of 2-(1,3-Bis(N-butyl-imidazol-2-ylidene)phenylene)(chloro) palladium (II)

1,3-Bis(1-butylimidazolium-3-yl)benzene dichloride (0.425 g, 1.07 mmol), tetrakis(dimethylamino)zirconium (0.431 g, 1.61 mmol), and $CH_2Cl_2$ (40 ml) were stirred for 1 hr at room temperature yielding a clear, pale yellow solution. $PdCl_2(PhCN)_2$ (0.412 g, 1.07 mmol) was added and stirring was continued at room temperature for 8 hrs yielding a clear, yellow solution. Distilled water (0.5 ml) was added and stirred for 10 min. Filtration and concentration afforded a yellow solid. The solid was washed with acetone and precipitated from $CH_2Cl_2$ with hexanes to give a pale yellow solid (0.283 g, 57%). $^1$H NMR (300.130 MHz, $CD_2Cl_2$): δ 7.38 (d, J=1.5 Hz, 2H), 7.15 (t, J=7.7 Hz, 1H), 6.95 (d, J=1.6 Hz, 2H), 6.93 (d, J=7.9 Hz, 2H), 4.67 (t, J=7.3 Hz, 4H), 1.84 (quintet, J=7.4 Hz, 4H), 1.44 (sextet, J=7.5 Hz, 4H), 0.97 (t, J=7.4 Hz, 6H); $^{13}C\{^1H\}$ (75.47 MHz, $CD_2Cl_2$): δ 177.5, 146.7, 145.0, 125.4, 120.6, 115.0, 108.5, 49.9, 34.2, 20.2, 14.2; MS (ESI) m/z 427.2 ($M^+$-Cl calcd for $C_{20}H_{25}N_4Pd$. 427.8593) Predicted for $C_{20}H_{25}N_4Pd$: 427.11 (100%), 429.11 (95.9%), 426.11 (81.2%), 431.11 (42.6%). Experimental for $C_{20}H_{25}N_4Pd$: 427.1 (93.2%), 429.1 (95.9%), 426.1 (82.3%), 431.1 (46.4%); Anal. Calcd for $C_{20}H_{25}N_4PdCl\cdot0.5\ H_2O$: C, 50.86; H, 5.55; N, 11.86. Found: C, 50.54; H, 5.22; N, 11.68.

Complex 2: Synthesis of 2-(1,3-Bis(N-butyl-imidazol-2-ylidene)phenylene)(bromo) palladium (II)

1,3-Bis(1-butylimidazolium-3-yl)benzene dibromide (0.375 g, 0.826 mmol), tetrakis(dimethylamino)zirconium (0.311 g, 1.2 mmol), and THF (20 ml) were stirred for 1 hr at room temperature yielding a bright yellow solution. $PdBr_2(PhCN)_2$ (0.366 g, 0.826 mmol) was added and stirring was continued at room temperature for 8 hrs yielding a cloudy orange solution. After standing for 10 min, a grey precipitate was observed with a clear orange supernatant liquid. The precipitate was collected and $CH_2Cl_2$ (10 ml) was added to it. The solution was filtered and concentrated, yielding a slightly yellow-orange solid. The solid was washed with acetone, yielding a white solid (0.157 g, 40%). X-ray quality crystals were grown by slow diffusion of diethyl ether vapor into a saturated $CH_2Cl_2$ solution of 2 (0.102 g, 49%). $^1$H NMR (300.130 MHz, $CD_2Cl_2$): δ 7.38 (d, J=1.9 Hz, 2H), 7.17 (psuedo t, 1H), 6.96 (d, J=2.4 Hz, 2H), 6.94 (d, J=8.1 Hz, 2H), 4.73 (t, J=7.4 Hz, 4H), 1.86 (m, 4H), 1.46 (sextet, J=7.5 Hz, 4H), 0.97 (t, J=7.4 Hz, 6H); $^{13}C\{^1H\}$ (75.47 MHz, DMSO): δ 174.8, 145.5, 144.0, 125.3, 121.4, 115.6, 108.7, 48.8, 33.3, 19.1, 13.8; MS (ESI) m/z 427.2 ($M^+$-Br calcd for $C_{20}H_{25}N_4Pd$. 427.8593) Predicted for $C_{20}H_{25}N_4Pd$: 427.11 (100%), 429.11 (82.9%), 426.11 (75.9%), 431.11 (37.8%). Experimental for $C_{20}H_{25}N_4Pd$: 428.7 (100%), 426.8 (94.0%), 425.85 (67.2%), 430.75 (30.3%); Anal. Calcd for $C_{20}H_{25}N_4PdBr$: C, 47.31; H, 4.96; N, 11.03. Found: C, 47.20; H, 5.06; N, 10.80.

Complex 3: Synthesis of 2-(1,3-Bis(N-butyl-imidazol-2-ylidene)phenylene)(chloro) platinum (II)

1,3-Bis(1-butylimidazolium-3-yl)benzene dichloride (0.197 g, 0.5 mmol), tetrakis(dimethylamino)zirconium (0.168 g, 0.63 mmol) and $CH_2Cl_2$ (ca. 4 ml) were combined. The mixture was stirred for 1 hr at room temperature to afford a red homogenous solution. [Pt(COD)$Cl_2$] (0.187 g, 0.5 mmol) was added and stirring continued vigorously at room temperature for another 6 hr. The reaction mixture was transferred to a round bottom flask which contained 1 ml of distilled water, and the precipitate was removed by filtration. The filtrate was concentrated under vacuum to afford a yellow solid. The solid was washed with water, cold $CH_2Cl_2$, $Et_2O$, and was dried under vacuum yielding yellow crystalline solid (0.132 g, 49.6%). X-ray quality crystals were grown by slow diffusion of diethyl ether vapor into a saturated $CH_2Cl_2$ solution of 3. $^1$H NMR ($CD_2Cl_2$; 300.132 MHz): δ 7.40 & 7.01 (dd, 2H each, J=2 Hz, J=9 Hz, imi), 7.16 (t, 1H, J=7.8 Hz, p-Ph), 6.93 (dt, 2H, J=8 Hz, $J^4$ Pt—H=8.6 Hz, m-Ph), 4.69 (t, 4H, J=7.3 Hz, $NCH_2$), 1.86 (quintet, 4H, J=7.5 Hz), 1.45 (sextet, 4H, J=7.7 Hz), 0.97 (t, 6H, J=7.4); $^{13}$C NMR (d-DMSO; 75.476 MHz, 350K): δ 171.7 ($J^1$ Pt—C=1168 Hz), 144.1, 133.8 ($J^1$ Pt—C=937 Hz), 123.3, 121.1, 115.7, 107.6, 47.7, 32.7, 18.8, 13.2; ESI-MS: Calculated for $C_{20}H_{25}ClN_4PtNa$ [M+Na] (m/z): 575 (100%), 574 (93%), 573 (74%), 576 (45%), 577 (42%). Found: 575.2 (100%), 574.2 (96%), 573.2 (78%), 576.2 (46%), 577.2 (43%); Elemental analysis: Calculated: C, 43.52; H, 4.57; N, 10.15. Found: C, 43.19; H, 4.09; N, 9.90.

Complex 4: Synthesis of 2-(1,3-Bis(N-butyl-imidazol-2-ylidene)phenylene)(bromo) platinum (II)

1,3-Bis(1-butylimidazolium-3-yl)benzene dibromide (0.484 g, 1.0 mmol), tetrakis(dimethylamino)zirconium (0.321 g, 1.2 mmol), and THF (10 ml) were stirred for 1 hr at room temperature yielding a cloudy suspension. [Pt(COD)$Br_2$] (0.463 g, 1.0 mmol) was added and stirring was continued at room temperature for 8 hrs yielding a cloudy yellow solution. After standing for 10 min, a yellow precipitate was observed with a clear reddish supernatant liquid. The precipitate was collected and washed with toluene (3 ml×3), yielding an analytically pure yellow solid (0.242 g, 52.3%). Some of the solid was directly used for X-ray crystallography. $^1$H NMR ($CD_2Cl_2$; 300.132 MHz): δ 7.40 & 7.01 (dd, 2H each, J=2 Hz, J=9 Hz, imi), 7.18 (t, 1H, J=7.8 Hz, p-Ph), 6.93 (dt, 2H, J=8 Hz, $J^4$Pt—H=8.6 Hz, m-Ph), 4.76 (t, 4H, J=7.3 Hz, $NCH_2$), 1.87 (quintet, 4H, J=7.5 Hz), 1.45 (sextet, 4H, J=7.7 Hz), 0.97 (t, 6H, J=7.4 Hz); $^{13}$C NMR (d-DMSO; 75.476 MHz, 350K): δ 170.5 ($J^1$ Pt—C=1166 Hz), 143.8, 134.0 ($J^1$ Pt—C=953 Hz), 122.8, 121.3, 115.4, 107.5, 48.3, 32.8, 18.6, 13.1; ESI-MS: Calculated for $C_{20}H_{25}BrN_4Pt$ [M+] (m/z): 595.1 Found: 595.0; Elemental analysis: Calculated: C, 40.28; H, 4.22; N, 9.39. Found: C, 40.74; H, 4.33; N, 9.39.

Figure 1:
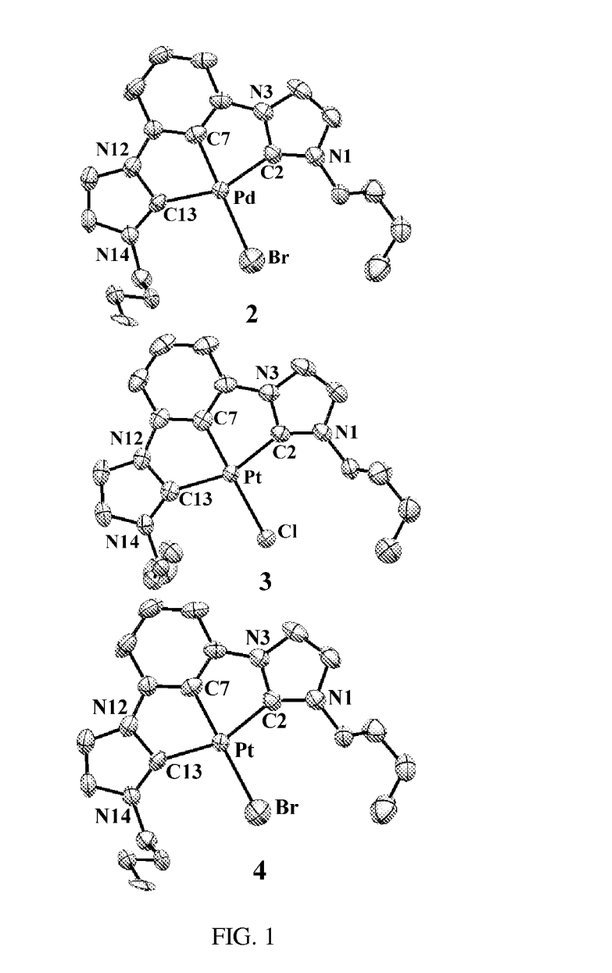
FIG. 1 depicts an ORTEP diagram of molecular structures of $CCC^{Bu}$-NHC-M(II)-X complexes for palladium and platinum.

X-ray quality crystals were obtained from the reaction (4), or by slow diffusion of $Et_2O$ into a $CH_2Cl_2$ solution (2 and 3). As will be appreciated from this FIG. 1, the molecular structure of $CCC^{Bu}$-NHC-M(II)-X complexes 2-4 was found to be distorted square planar at the metal center, which is very common for four-coordinate Pt(II) and Pd(II) complexes.[20] This figure shows ORTEP diagrams of the molecular structures of (50% thermal ellipsoids) of CCC$^{Bu}$-NHC—Pd(II)—Br 2, Pd—C7=1.937(8), Pd—C2=2.042(8), Pt—C13=2.043 (8) and Pd—Br=2.4551(15) Å; CCC$^{Bu}$-NHC—Pt—Cl 3, Pt—C7=1.941(3), Pt—C2=2.030(3), Pd—C13=2.035(3) and Pt—Cl=2.3997(7) Å; and CCC$^{Bu}$-NHC—Pt—Br 4, Pt—C7=1.955(6), Pt—C2=2.037(6), Pt—C13=2.036(6) and Pt—Br=2.5028(8) Å. Hydrogen atoms omitted for clarity. The C7-M-X atoms were linear (2: 179.0(2)°; 3: 179.40(8)°; 4: 178.66(18)°, and the C2-M-C13 angles were bent due to ligand constraints (2: 156.9(3)°; 3: 157.44(11)°; 4: 157.3(2)°. The M-C(NHC) bonds (M-C2 and M-C13) are about 5% longer than the M-C(aryl) bond. All the metal-carbon bond lengths fall into the usual range of reported structures.[19a,20b,21]

Figure 2A:
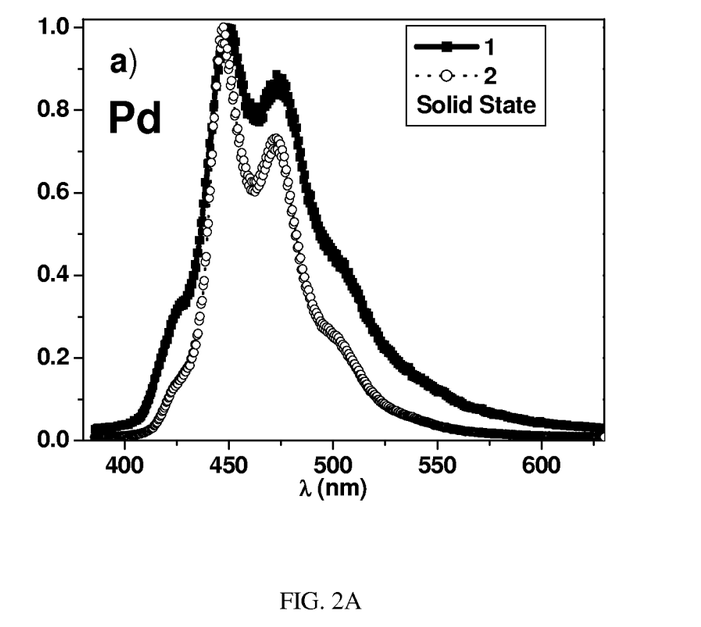
FIGS. 2A and 2B depict graphs of emission data of $CCC^{Bu}$-NHC-M(II)-X complexes in solid state at 298K (irradiated at 355 nm): a) 1 and 2, b) 3 and 4.
Figure 2B:
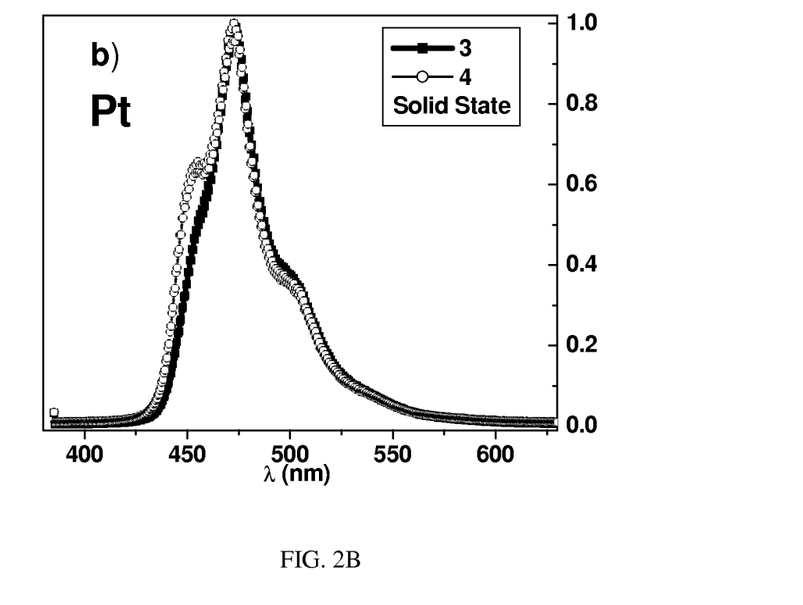
Figure 3:
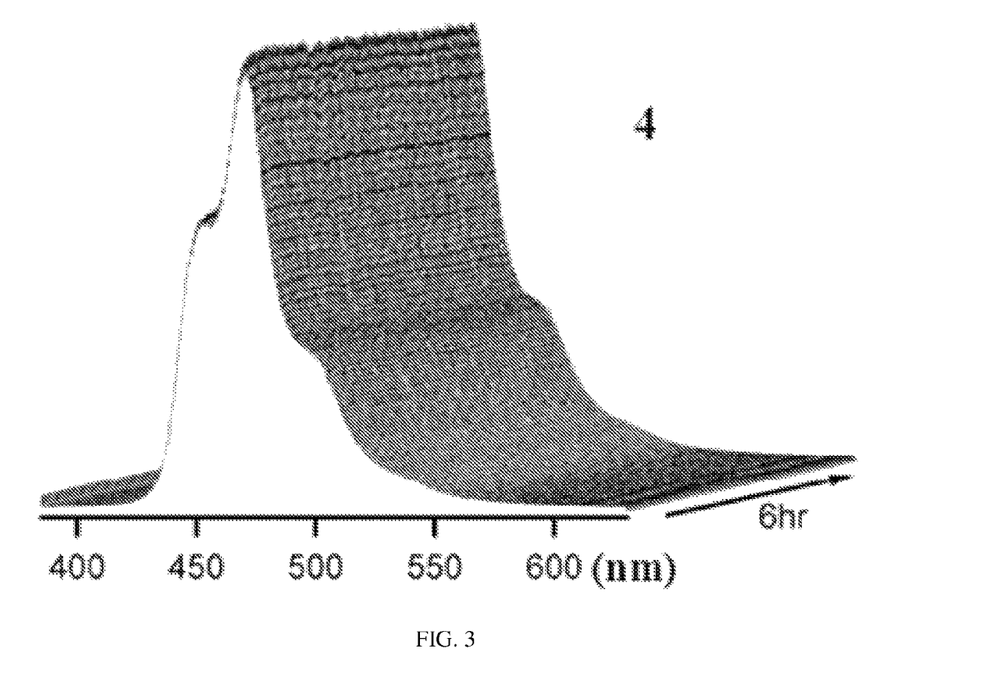
FIG. 3 depicts a graph of the time dependence of emission of solid state 4 in air over 6 hrs. and irradiated at 355 nm.

Photophysical Studies: Complexes 1-4 were found to emit blue light under appropriate UV stimulation. The absorption and emission data are reported in Tables 1 and 2, and FIGS. 2-4. Notably, in the solid state, the strong blue emissions of complexes 1-4 vary only slightly. For Pd complexes 1 or 2, $\lambda_{max}$ is ~449 nm, while $\lambda_{max}$ for Pt complexes 3 or 4 is 472 nm (FIG. 2A and FIG. 2B and Table 1). The red shift is ascribed to the heavy atom effect.[22] The excited state lifetimes of complexes 1-4 in the solid state vary from 1.7 to 5.2 μs (Table 1), which are comparable to other known organometallic complexes.[23]

TABLE 1

Emission and lifetime data of CCC$^{Bu}$-NHC-M(II)-X complexes 1-4 in solid state.

| | $\lambda_{em}$/nm (relative int.) [a] | % rentention [b] | $\tau_{obs}$/μs |
|---|---|---|---|
| 1 | 428 (34), 449 (100), 472 (89) | 94 | 5.2 |
| 2 | 427 (27), 448 (100), 473 (62) | 98 | 2.3 |
| 3 | 445 (39), 472 (100), 502 (42) | 99 | 1.7 |
| 4 | 455 (66), 472 (100), 502 (33) | 97 | 1.9 |

[a] Irradiated at 355 nm.
[b] Intensity of $\lambda_{max}$ over 6 h of continuous excitation.

The emissions of complexes 1-4 were stable in ambient atmosphere over extended periods. Time resolved emission spectrum of CCC$^{Bu}$-NHC—Pt—Br 4 is presented in FIG. 3. The authentic blue $\lambda_1$ (472 nm) of complex 3 retains 99% intensity while Complex 4 retains 97% intensity over 6 hrs continuous irradiation. Complexes 1 (94%) and 2 (98%) give similar stability with a more violet $\lambda_{max}$ (~449 nm). These data indicate that the complexes do not decompose in air with UV irradiation. Most organometallic emitters, reported to date, were handled and tested in an inert atmosphere or under vacuum, which usually increases the cost of fabrication and limits the application of the devices.[24]

Figure 4A:
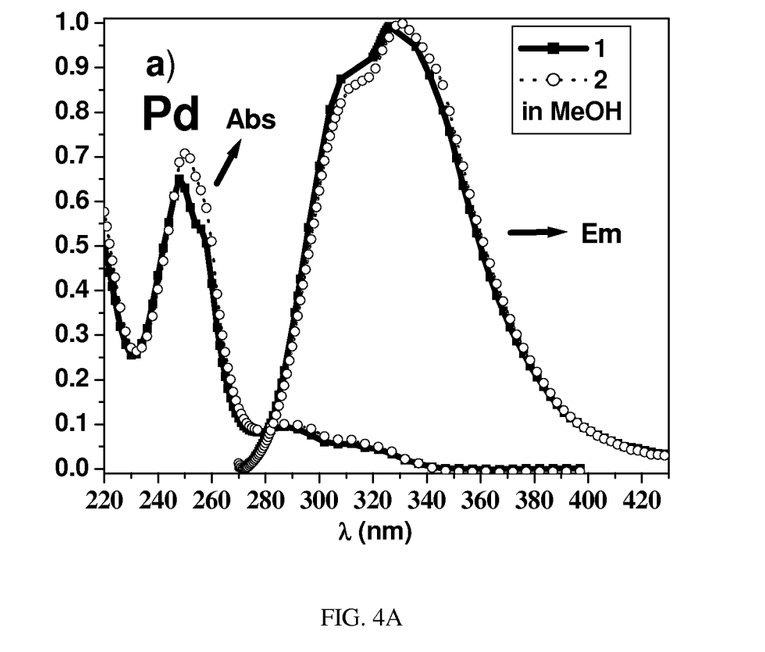
FIG. 4A and FIG. 4B depict graphs of emission data of $CCC^{Bu}$-NHC-M(II)-X complexes in MeOH solution: a) Pd complexes 1 and 2 (irradiated at 230 nm), b) Pt complexes 3 and 4 (irradiated at 360 nm).
Figure 4B:
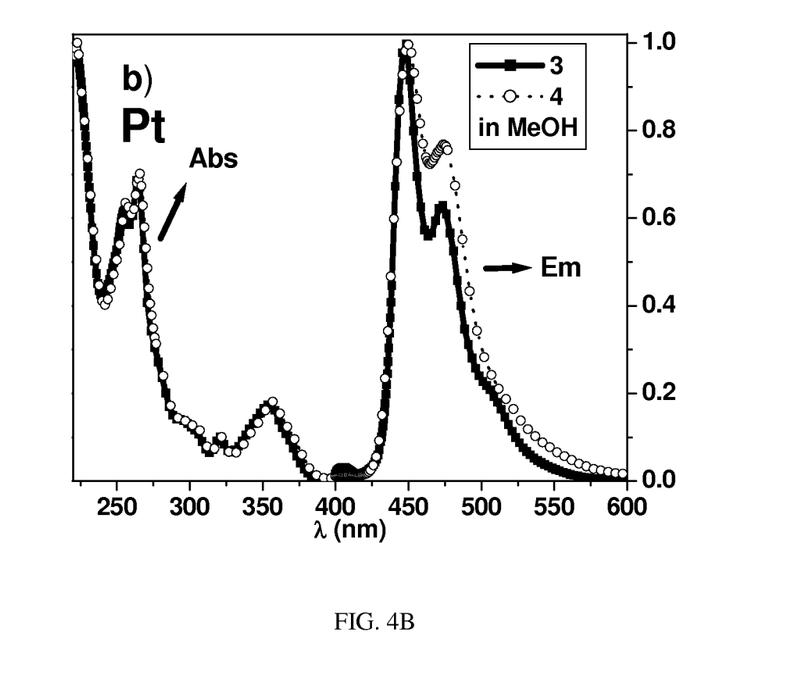

In MeOH solution, significant differences were observed in the spectra. Pd complex 1 or 2 both exhibit a major absorption peak around 250 nm that tails to ~350 nm (FIG. 4A). Pt complex 3 or 4 both show their most intense absorption around 265 nm and minor peaks near 323 and 355 nm (FIG. 4B). A similar red shift from Pd to Pt was observed in the solution emission spectra of 1 or 2 (~311 nm and ~330 nm, FIG. 4A and Table 2) vs. 3 or 4 (~445 nm and ~470 nm, FIG. 4B and Table 2). Observed solution quantum efficiency data of complexes 1-4 falls in the range of 0.6-2.2% (Table 2). This data is comparable to organometallic complexes of similar structure.[25] The solution emissions of these structurally similar complexes occur over a broad range from UV to violet to blue.

TABLE 2

Photophysical properties of CCC$^{Bu}$-NHC-M(II)-X complexes 1-4 in MeOH solution.

| | $\lambda_{abs}$/nm ($\epsilon \times 10^{-3}$ M$^{-1}$ cm$^{-1}$) | $\lambda_{em}$/nm (relative int.) | $\Phi_{obs}$/% |
|---|---|---|---|
| 1 | 248 (32.6), 287 (4.8) | 311 (90), 328 (100) [a] | 2.21 [b] |
| 2 | 251 (41.9), 286 (5.9) | 311 (85), 330 (100) [a] | 1.23 [b] |
| 3 | 265 (22.9), 323 (3.3), 355 (5.7) | 445 (100), 469 (75) [c] | 0.59 [d] |
| 4 | 266 (24.0), 323 (3.5), 358 (6.2) | 445 (100), 470 (76) [c] | 0.63 [d] |

[a] Irradiated with 230 nm.
[b] Referenced to L-(−)-tyrosine.
[c] Irradiated with 360 nm.
[d] Referenced to quinine sulfate.

Complexes of Group 10 Metals.

Our metallation/transmetallation methodology has been extended to the group 10 metal Ni. Initial experiments employed a diiodide ligand precursor and a chloride metal source similar to the conditions for group 9 metals. Imidazolium salt 5a was combined with 1.5 eq. Zr(NMe$_2$)$_4$ and stirred for 1 hr, at which point NiCl$_2$(glyme) was added and reacted for 16 hr (Scheme 2). The $^1$H NMR showed broad peaks for all product proton signals following aqueous workup. This broadening of the spectrum was attributed to rapid exchange of chloride and iodide ligands in the coordination sphere of the complex. Previous work has shown no issues with rapid halogen exchange for zirconium, rhodium, or iridium metal centers using this ligand set.[22-24] In each of these cases, the metals preferentially bind the softer iodide in favor of the chloride. The rapid exchange of halogens on the NMR timescale is likely a product of the square planar geometry of the complex combined with the strong trans effect of the central phenyl donor. This labilizes the halide ligand allowing for interconversion between chloride and iodide.

To address this issue of halogen exchange, halide matching of the ligand precursor and the metal source was explored. Using the dichloride ligand precursor to generate the zirconium intermediate followed by addition of NiCl$_2$(glyme) resulted in sharp lines in the $^1$H NMR spectrum (Scheme 2; 6a→6). A dibromide ligand precursor and a bromide containing nickel source, NiBr$_2$(glyme), were allowed to react for 16 hours in an attempt to synthesize complex 3 (Scheme 2; 7a→7). The $^1$H NMR spectrum showed broadening of the N$_{imid}$—CH$_2$ signal of the butyl chain at this reaction time. This was an unexpected result as the halogens for the ligand precursor and metal source were matched as they were in the chloride system. It was suspected that the dimethyl amido ligands present for deprotonation of the ligand precursor were reacting with the solvent, dichloromethane, over long reaction times. Shortening the reaction time to 4 hours after the generation of the zirconium intermediate resulted in peak resolution similar to that found for the chloride. This indicates that chloride is being extracted from the solvent, likely by the dimethyl amido ligands of the zirconium source, at long reaction times causing similar, albeit decreased, effects to reaction conditions employing mixed halogen reagents.

Scheme 2

5a: X = I; R = Bu
6a: X = Cl; R = Bu
7b: X = Br; R = Bu
8c: X = Cl; R = Bn

5: X = I/Cl; R = Bu
6: X = Cl; R = Bu
7: X = Br; R = Bu
8: X = Cl; R = Bn

Ni Complex 2: Synthesis of 1,3-bis(1-butylimidazolene-3-yl)benzenenickel (II) chloride 1,3-Bis(1-butylimidizol-3-yl)benzene dichloride (0.282 g, 0.717 mmol) and $Zr(NMe_2)_4$ (0.288 g, 1.08 mmol) were combined in $CH_2Cl_2$ (30 mL) under inert atmosphere and stirred for 1 hour. $NiCl_2$(glyme) (0.174 g, 0.789 mmol) was added with stirring to dissolve. Water (0.600 mL, 0.033 mol) was added and stirred vigorously for 5 min producing a precipitate that was removed and washed with $CH_2Cl_2$ (3×10 mL). The filtrate was concentrated, and the resulting orange-yellow solid was dried under vacuum (0.252 g, 84%). X-ray quality crystals were grown from an $EtOH/CH_2Cl_2$ (4:1) solution of 2 by slow evaporation. $^1H$ NMR (300 MHz, $CD_2Cl_2$): δ 7.27 (d, 2H, J=1.9), 7.05 (t, 1H, J=7.7), 6.83 (d, 2H, J=1.9), 6.74 (d, 2H, J=7.7), 4.61 (t, 4H, J=7.4), 1.82 (quin, 4H, J=7.5), 1.41 (sext, 4H, J=7.5), 0.96 (t, 6H, J=7.4). $^{13}C\{^1H\}$ (75 MHz, $CD_2Cl_2$): δ 172.3, 146.9, 145.5, 124.6, 121.8, 112.9, 106.5, 48.7, 34.0, 19.7, 13.7. $[M-Cl]^+$ (m/z): 379. $[M-Cl+MeCN]^+$ (m/z): 420. Anal. Calcd (%) for $C_{20}H_{25}ClN_4Ni$: C, 57.80; H, 6.06; N, 13.48. Found: C, 57.63; H, 5.77; N, 13.32.

Ni-Complex 3: Synthesis of 1,3-bis(1-butylimidazolene-3-yl)benzenenickel (II) bromide 1,3-Bis(1-butylimidizol-3-yl)benzene dibromide (0.316 g, 0.654 mmol) and $Zr(NMe_2)_4$ (0.261.6 g, 0.981 mmol) were combined in $CH_2Cl_2$ (30 mL) under inert atmosphere and stirred for 1 hour. $NiBr_2$(glyme) (0.222 g, 0.719 mmol) was added with stirring to dissolve for 3 hours. Water (0.300 mL, 0.0167 mol) was added producing a precipitate that was removed and washed with $CH_2Cl_2$ (3×10 mL). The filtrate was concentrated, and the resulting orange-yellow solid was dried under vacuum (0.190 g, 63%). $^1H$ NMR (300 MHz, $CD_2Cl_2$): δ 7.27 (d, 2H, J=1.8), 7.06 (t, 1H, J=7.7), 6.83 (d, 2H, J=1.8), 6.75 (d, 2H, J=7.7), 4.66 (t, 4H, J=7.4), 1.83 (quin, 4H, J=7.6), 1.42 (sext, 4H, J=7.4), 0.97 (t, 6H, J=7.3). $^{13}C\{^1H\}$ NMR (75 MHz, $CD_2Cl_2$): δ 172.1, 146.8, 145.9, 124.8, 122.0, 112.9, 106.6, 49.5, 34.2, 19.7, 13.6. $[M-Br]^+$ (m/z): 379. $[M-Br+MeCN]^+$ (m/z): 420. Anal. Calcd (%) for $C_{20}H_{25}BrN_4Ni$ C, 52.22; H, 5.48; N, 12.18. Found: C, 52.35; H, 5.34; N, 12.11.

Ni-Complex 4: Synthesis of 1,3-bis(1-benzylimidazolene-3-yl)benzenenickel (II) chloride, 4

1,3-Bis(1-benzylimidizol-3-yl)benzene dichloride (0.288 g, 0.621 mmol) and $Zr(NMe_2)_4$ (0.248 g, 0.932 mmol) were combined in $CH_2Cl_2$ (30 mL) under inert atmosphere and stirred for 1 hour. $NiCl_2$(glyme) (0.150 g, 0.683 mmol) was added and stirred for 3 hours. Water (0.600 mL, 0.033 mmol) was added producing a precipitate that was removed and washed with $CH_2Cl_2$ (3×10 mL). The filtrate was concentrated, and the resulting orange-yellow solid was dried under vacuum (0.294 g, 98%). $^1H$ NMR (300 MHz, $CD_2Cl_2$): δ 7.47 (d, 4H), 7.34 (m, 8H), 7.08 (t, 1H), 6.79 (d, 4H), 5.95 (s, 4H). $^{13}C\{^1H\}$ NMR (75 MHz, $CD_2Cl_2$): δ 174.47 (C, $C_{NHC}$), 148.8, 147.3, 139.5, 130.6, 130.0, 129.7, 126.8, 123.7, 115.7, 108.8 (C/CH, $C_{Ar}$), 53.9 ($CH_2$, Bn). $[M-Cl]^+$ (m/z): 447. $[M-Cl+MeCN]^+$ (m/z): 488. Anal. Calcd (%) for $C_{26}H_{21}N_4NiCl$: C 64.57; H, 4.01; N, 11.30. Found: C, 63.92; H, 4.40; N, 11.33.

Evaluation and comparison of $^1H$ NMR data to known compounds, gives further evidence for the correct identification of these complexes. We have previously reported a CCC-NHC Zr pincer complex[22] that exhibits two broad singlets at 4.44 and 4.32 for the $N_{(imid)}$—$CH_2$ group of the butyl chain. Upon transmetallation to nickel, a downfield shift was observed for these protons, comparable to what has been previously reported for the analogous late transition metal Ir complex[23].

Figure 5:
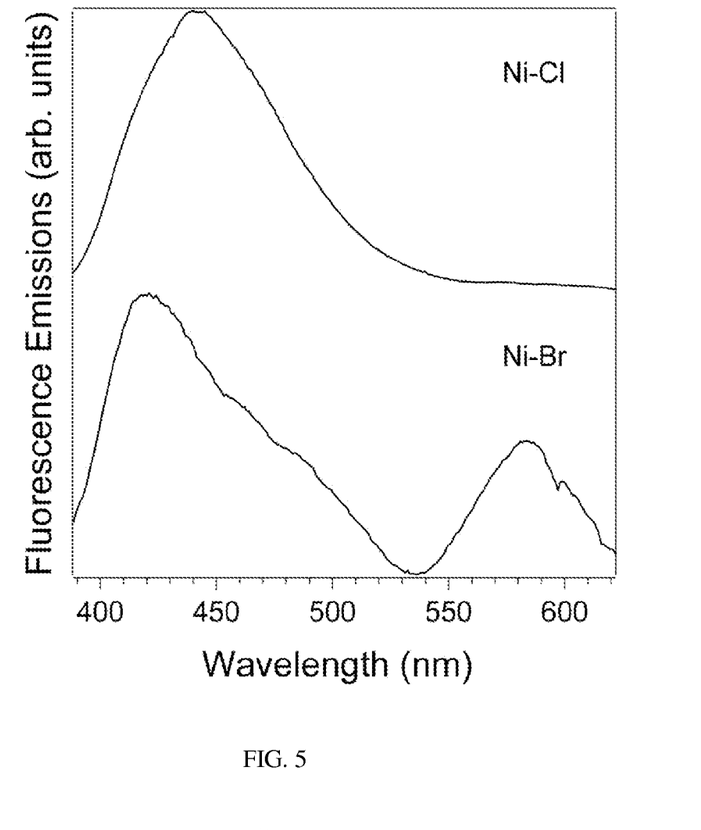
FIG. 5 depicts a graph of Fluorescence spectra of Ni-Complex 2 and Ni-Complex 3.
Figure 6:
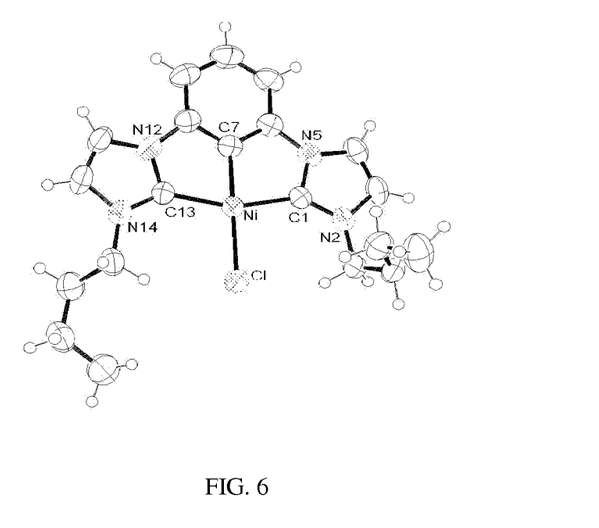
FIG. 6 depicts an ORTEP diagram of Ni-Complex 2.

A number of organometallic complexes have been found to fluoresce, giving them interesting potential for use as organic light emitting diodes (OLEDs). Because fluorescent organometallic complexes can have their fluorescent intensities and emission wavelengths altered when other ligands coordinate, they can serve as sensors for molecules that can coordinate the metal. They can also be used as switches when exposed to redox conditions or pH changes that turn their photoluminescent properties on and off. Based on this, preliminary solid state fluorescence spectra were collected for complexes 2 and 3 (FIG. 5) showing violet region emission with 2 having $\lambda_{max}$=440 nm and 3 having $\lambda_{max}$=420 nm. For the acquisition of solid state fluorescence spectra, samples were excited using 355+/−5 nm light from a 500 W Xe lamp and monochromator. Fluorescence emission was collected using a fiber optic cable, was dispersed using a Princeton Instruments/Acton spectrograph, and detected with a water-cooled Princeton Instruments Photodiode Array detector.

The structure of Ni-Complex 2 was determined using X-ray crystallography. Table 3 compares M—C bonds and $C_{NHC}$-M-$C_{NHC}$ angles of 2 with previously reported CCC-NHC Rh and Ir complexes of the same ligand.[22,23] Ni-Complex 2 exhibits a distorted square planar coordination geometry with a pincer coordination similar to those of the previously reported complexes of the Zr, Rh, and Ir. The shortening of the bond lengths and widening of the $C_{NHC}$—Ni—$C_{NHC}$ bond angle is likely a result of the decrease in the metal's size. Table 4 summarizes selected bond lengths and angles of 2 and previously reported CNC, PNP, and PCP pincer analogues.[27-31] Ni-Complex 2 generally resembles the CNC analogues reported by Inamoto with the differences being longer metal-carbene bonds, longer metal-chloride and shorter metal-aryl bonds, and a tighter aryl-metal-chloride bond angle. The metal-aryl bond is shorter and metal-chloride bond is longer than the corresponding bonds of nearly all of the analogous pincer complexes. The carbene-metal-carbene angle is wider and the aryl-metal-chloride angle tighter than any of the analogous PCP/PNP pincers. Table 5 summarizes selected bond angles of Ni-Complex 2 and the monocationic CCC pincer reported by Chen containing fused 5- and 6-memebered metallacycles.[32] As with the CNC pincers, Ni-Complex 2 has longer metal-carbene bonds than the CCC homologue, and the metal-aryl bond of 2 is shorter than the corresponding metal-vinyl bond.

Thin Film Applications:

The disclosed complexes herein may further be used in the creation of thin films. Polymethylmethacrylate (PMMA) is suitable as a transparent supporting matrix for light emitting material. In one embodiment, a blue emitters (CCCBu-NHC—Pt—Cl) was incorporated into the matrix, and a transparent thin film was fabricated.

PMMA        CCC$^{BU}$-NHC-Pt-Cl

Figure 7:
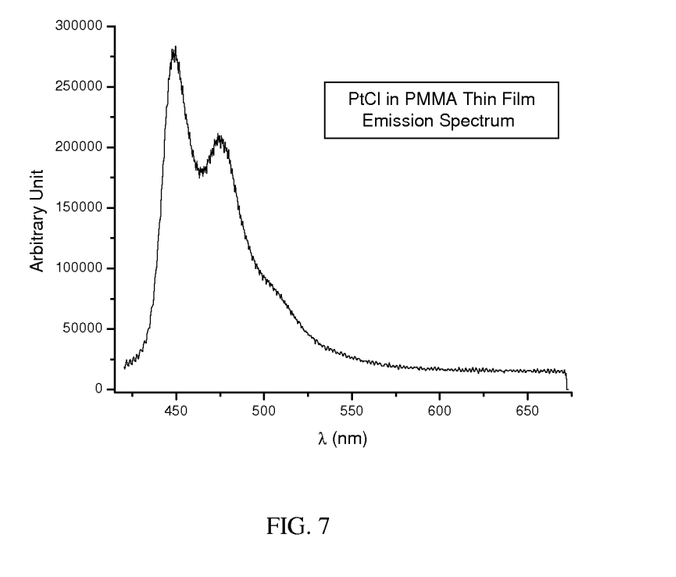
FIG. 7 depicts the emission spectrum of a thin film made from a platinum complex.

Detailed description of the procedure used in creating the thin film. CCC$^{Bu}$-NHC—Pt—Cl (0.1 mg, 0.18 μmol), PMMA powder (250 mg) and ca. 4 mL CH$_2$Cl$_2$ were added in an agate mortar. The mixture was then grounded for 15 min. The transparent slurry was then spread on a clean and even surface. The transparent thin film was obtained when the slurry was dried in air. The emission spectrum of this thin film can be seen in FIG. 7.

1,8-Anthracene Bridged Bis-NHC Pincer Complexes as Light Emitters.

The aryl-bridged bis-NHC ligands are of two major classes depending on the atoms making the bonds to the metal: CCC-NHC pincer complexes and CNC-NHC pincer complexes. To date, most of this type of complexes adopt a single aromatic ring bridge (phenyl-bridged,[2] xylylenyl-bridged,[3] pyridylenyl-bridged[4] and 2,6-lutidenyl-bridged[5]). While there are very limited examples of fused aromatic rings bridged pincer complexes.[6] We have recently synthesized an anthracene-bridged bis-imidazole pincer ligand and metalated it with Zr and Rh.

M-BIA analogs wherein R is a hydrogen, alkyl or aryl group that may contain heteroatoms, or a heteroatom substituent, R$^1$ is an alkyl or aryl group that may contain heteroatoms, the structures indicated by the dashed lines may be hydrogen or rings that may be aromatic or aliphatic fused rings, or alkyl or aryl groups that may contain heteroatoms, wherein M is selected from the group consisting of metals and metalloids, wherein L is a ligand, and x is any number between 0 and 3, and n is any number between 0 and 6, and m is any number between 0 and 4, and p is any number between 0 and 3.

Scheme 3:

1,8-Dibromoanthracene (2.84 g, 8.4 mmol, prepared according to literature), imidazole (1.93 g, 32 mmol), CuO (0.08 g, 1 mmol), potassium carbonate (5.28 g, 32 mmol) and DMSO (10 mL) were added to a round bottom flask. The solution was heated to 150° C. for 4 days. The reaction was then cooled to room temperature and filtered through basic alumina with methanol. The crude product was then dissolved in minimum amount of CH$_2$Cl$_2$ and pushed to precipitate with addition of hexanes. The precipitates were collected by filtration and washed with hexanes for 3 times, yielding 1.1 g (42%) of 1,8-bisimidazoliumanthracene (BIA).

$^1$H NMR (300.130 MHz, CDCl$_3$): δ 8.64 (s, 1H, H$_{10}$), 8.13 (d, J=8.7 Hz, 2H, H$_4$ and H$_5$), 8.02 (s, 1H, H$_9$), 7.71 (s, 2H, H$_{imi}$), 7.57 (t, J=6.9 Hz, 2H, H$_3$ and H$_6$), 7.47 (d, J=6.9 Hz, 2H, H$_2$ and H$_7$), 7.24 (s, overlapped with solvent, 2H, H$_{imi}$), 7.19 (s, 2H, H$_{imi}$).

Scheme 4:

BIA

BIA-Hex/I 1,8-Bisimidazoliumanthracene (100 mg, 0.325 mmol), 1-iodohexane (354 mg, 1.7 mmol) and acetonitrile (50 mL) were added to a schlenk tube. The reaction mixture was heated to 100° C. for 5 days. The volatile components were then removed under vacuum. The crude product was washed with cold $CH_2Cl_2$ three times yielding 152 mg (64%) of 1,8-bis(1-hexylimidazolium-3-yl) anthracene diiodide (BIA-Hex/I).

$^1$H NMR (300.130 MHz, $CDCl_3$): δ 9.79 (s, 2H, $H_{imi}$), 9.15 (s, 1H, $H_{10}$), 8.53 (d, J=7.8 Hz, 2H, $H_4$ and $H_5$), 8.33 (s, 2H, $H_{imi}$), 8.12 (s, 2H, $H_{imi}$), 8.02-8.00 (m, 3H, $H_2$, $H_7$ and $H_9$), 7.86 (dd, J=6.9 Hz, J=6.9 Hz, 2H, $H_3$ and $H_6$), 4.28 (t, J=7.5 Hz, 4H), 1.93 (m, 4H), 1.35-1.23 (m, 12H), 0.90 (s, br, 6H). ESI-MS: [M-I]$^+$ C32H40N4I calculated: 607.59. found: 606.95

Scheme 5:

Rh-BIA

Zr-BIA: 1,8-Bis(1-hexylimidazolium-3-yl) anthracene diiodide (0.004 g, 0.005 mmol), tetrakis(dimethylamino)zirconium (0.0037 g, 0.0012 mmol), and $CD_2Cl_2$ (0.4 ml) were combined in a screw capped NMR tube at room temperature yielding a clear yellow solution.

$^1$H NMR (300.130 MHz, $CD_2Cl_2$): δ 8.77 (s, br, 1H), 8.24 (s, br, 2H), 7.69-7.15 (br, 8H), 4.42 (s, br, 4H), 3.2-1.4 (multiple peaks overlapped with impurities), 0.99 (t, J=6.6 Hz, 6H); Not isolated.

Rh-BIA: To the in situ generated Zr-BIA solution, [Rh(COD)Cl]$_2$ (0.003 g, .0.005 mmol) was added. The solution turned brown.

$^1$H NMR (300.130 MHz, $CD_2Cl_2$): δ 8.75 (s,), 8.63 (s, br), 8.54 (d, J=6.9 Hz), 8.25 (d, J=8.7 Hz), 7.74 (m), 7.48 (s), 7.23 (s), 7.13 (s), 7.00 (s), 6.92 (s), 4.72 (s, br), 4.33 (s, br), 3.4-0.5 (multiple peaks overlapped with impurities); $^{13}$C NMR ($CD_2Cl_2$; 125.758 MHz,): δ 184.7 (J$^1$ Rh—C=48 Hz), 135.9, 131.8, 129.3, 128.2, 125.2, 124.1, 120.2, 119.9, 95.7-13.9 (m, mixed with excess [Rh(COD)Cl]$_2$); Not isolated.

Abnormal Pincer Carbenes Complexes as Light Emitters

The discovery of isolable carbenes by Bertrand[1] and Arduengo[2] has lead to the enormous increase in the study of carbenes, particularly N-Heterocyclic carbenes (NHCs), seen over the past two decades[3-7]. NHC have now become ubiquitous as ancillary ligand for numerous catalyses[8-10]. Although NHC have been well studied when bound to a metal via the C2 carbon, the chemistry of NHC's binding though the C4 or C5 backbone ("abnormal" carbenes) is still in its infancy. Currently, late transition metal "abnormal" carbene complexes make up the bulk of what has been reported[11]. The majority of the reported "abnormal" carbenes are simple monodentate ligands[11-16] or are tethered with another neutral donor such as pyridyl[17,18], phosphine[19-21] or another "abnormal" carbene[22-24] functionality to facilitate binding to the late transition metal. We have previously reported a tridentate CCC-NHC pincer ligand system, which is metallated with the use of an early transition metal amido reagent. It can be transmetallated to a late transition metal[25]. Based on this seminal work we have incorporated "abnormal" carbenes into the ligand architecture, to create an aC$^{NHC}$CaC$^{NHC}$ pincer ligand architecture generally illustrated in as such:

wherein R, R2 are selected from the group consisting of a hydrogen, alkyl or aryl group that may contain heteroatoms, R$^1$ is an alkyl or aryl group that may contain heteroatoms, R3 is selected from the group consisting of hydrogen, alkyl or aryl groups that may contain heteroatoms, including silicon, wherein M is selected from the group consisting of metals and metalloids, wherein L is a ligand, and x is any number between 0 and 3, and n is any number between 0 and 6.

Herein we report synthesis of an "abnormal" carbene a C$^{NHC}$CaC$^{NHC}$ pincer ligand precursor and its platinum complex.

Scheme 6:

R = Me

Illustrated in scheme 6 is the synthetic method of preparing the bis(2-methylimidazole) benzene. It is a slight modification of the previously reported methodology for the copper coupling of imidazole to Dibromobenzene[26,27]. 1,3 Dibromobenzene (5.9 mL, 48.7 mmol, 1 eq.), 2-methylimidazole (10 g, 121.8 mmol, 2.5 eq.) copper (II) oxide (0.38 g, 4.8 mmol, 0.1 eq), potassium carbonate (13.5 g, 97.4 mmol, 2 eq.) and dimethylsulfoxide (300 mL) were added to a round bottom flask. The solution was heated at 150° C. for 5 days. The reaction was then cooled to room temperature and diluted with 3 L of $CH_2Cl_2$. The diluted solution was then run through a column of basic alumina. 1 L of $CH_2Cl_2$ was then run through the column to extract residual product from the column. This solution was then concentrated down under vacuum. (15.15 g crude product, 130% crude yield). This crude product was then purified by silica gel chromatography using a 10:1 $CH_2Cl_2$:MeOH solution. 2.48 g of purified bisimidazole product (29% purified yield) was collected. An addition 4.56 g (39% yield) of monoimidazole product was also collect. This fraction was treated under similar conditions to produce more desired bisimidazole product.

$^1$H NMR ($CD_2Cl_2$) δ 7.62 (t, J=8 Hz, 1H), 7.38 (dd, $J_1$=8, $J_2$=2 Hz, 2H), 7.28 (t, J=2 Hz, 1H), 7.07 (d, J=1 Hz, 2H), 6.99 (d, J=1 Hz, 2H), 2.38 (s, 6H) $^{13}$C (500 MHz, $CD_2Cl_2$): δ 144.5, 139.1, 130.5, 128.0 124.8, 122.4, 120.4, 13.7 [M+] 238.8

Illustrated in scheme 7 is the alkylation of bis(2-methylimidazole) benzene to synthesize the imidazolium salt ligand precursor.

Scheme 7:

R = Me, R' = Bu

Analogous to the reported CCC-NHC ligand precursor synthesis[25], bis(2-methyl)imidazole benzene (50 mg, 0.21 mmol, 1 eq.), 1-iodobutane (0.96 mL, 8.40 mmol, 40 eq.), and acetonitrile (50 mL) were added to a round bottom flask. The solution was then refluxed at 110° C. for 16 h. The volatile were then removed under vacuum. This crude product was then dissolved in 25 mL $CH_2Cl_2$ and 50 mL of benzene was added to precipitate out the purified product. 70 mg purified product, 55% yield.

$^1$H NMR ($CD_2Cl_2$) δ 8.8 (s, 1H), 7.94 (m, 3H), 7.77 (d, J=2 Hz, 2H), 7.44 (d, J=2 Hz, 2H), 4.18 (t, J=8 Hz, 4H), 2.88 (s, 6H) 1.95 (quintet, J=8 Hz, 4H), 1.49 (sextet, J=7 Hz, 4H) 1.02 (t, J=7 Hz, 6H). $^{13}$C (300 MHz, $CD_2Cl_2$): δ 144.9, 135.5, 132.1, 128.7, 126.2, 122.8, 121.6, 49.5, 31.2, 19.8, 13.3, 13.0

Illustrated in scheme 8

Scheme 8:

R = Me, R' = Bu, R'' = H

This mechanism shows the metallation and transmetallation of the "abnormal" carbene $aC^{NHC}CaC^{NHC}$ pincer ligand precursor to synthesize the platinum $aC^{NHC}CaC^{NHC}$ pincer complex. This synthesis is also a slight modification of the previously reported metallation/transmetallation procedure to afford the CCC-NHC pincer Rh complex[25]. The bis(2-methyl)imidazolium Iodo salt (100 mg, 0.16 mmol, 1 eq.), Tetrakis(dimethylamido) Zirconium (IV) (220 mg, 0.824 mmol, 5 eq) and $CH_2Cl_2$ (50 mL) were added to a silated schlenk flask. The solution was stirred at room temp for 24 h. Diiodo(1,5-cyclooctadiene)platinum (II) (91.87 mg, 0.16 mmol, 1 eq.) was then added and the solution was stirred for another 24 h (Scheme 8). 5 mL of $H_2O$ was then added and the solution was stirred for 5 minutes to precipitate the Zirconium. The solution was then filter through a frit (fine grade) to remove precipitate zirconium. The $H_2O$ was then separated and extracted with $CH_2Cl_2$ (3×10 mL). The volatiles were then removed under vacuum. The product was then dissolved in $CH_2Cl_2$ (5 mL). Hexanes were then slowly added until a milky solution was seen. The milky solution was left for 30 minutes. The solution was then decanted into a clean round bottom flask and excess hexanes were added to precipitate out the product. The solid was collected on frit. Excess $CH_2Cl_2$ was run through the frit to collect the product in a new round bottom flask. The volatiles were removed under vacuum. 20 mg, 18% yield.

$^1$H NMR (CD$_2$Cl$_2$) δ 7.15 (s, 3H) 6.78 (s, 2H), 3.99 (t, J=7 Hz, 4H), 2.84 (s, 6H), 1.77 (quintet, J=7.5 Hz, 4H), 1.38 (sextet, 7 Hz, 4H), 0.96 (t, J=7 Hz, 6H). $^{13}$C{$^1$H} (500 MHz, CD$_2$Cl$_2$): δ 157.8, 148.2, 146.4, 140.7, 126.5 (t, J=101 Hz), 123.8, 113.6 (t, J=40 Hz), 49.1, 47.0, 34.0, 21.8, 15.2, 13.5

Triazole Complexes as Potential Light Emitters.

Triazoles have the following general structure:

R = alkyl or aryl (1-50 Carbons)
R$^1$ = H, alkyl, aryl, or heteroatom substituents, X => 0; or fused rings
R$^2$, R$^3$ = H, alkyl, aryl, or heteroatom substituents, symmetrical or unsymmetrical, (R, R$^2$, R$^3$) can form fused rings (aromatic or aliphatic)
M = any metal or metalloid of the periodic table
L$_n$ = is any generic, common ligand or substituent We disclose the use of triazoles as potential light emitters as well.

1,3-di-1-triazolebenzene preparation:

As can be seen from scheme 9 1,3-dibromobenzene (0.284 mL, 2.35 mmol), 1,2,4-triazole (0.407 g, 5.89 mmol), copper (II) oxide (0.045 g, 0.566 mmol), potassium carbonate (0.820 g, 5.93 mmol) and dimethylsulfoxide (5 mL) were added to a round bottom flask. The solution was heated at 150° C. for 48 hours. The reaction was then cooled to room temperature and diluted with 50 mL of dichloromethane. The diluted solution was then passed through a column of basic alumina. 20 mL of dichloromethane was then passed through the column to extract residual product from the column, and the filtrate was concentrated down under vacuum. The solid was washed with 5 mL of ethyl acetate. 0.31 g of purified product was collected. $^1$H NMR (DMSO) δ 9.43 (s, 2H), 8.39 (s, 1H), 8.31 (s, 2H), 7.93 (d, J=8 Hz, 2H), 7.76 (t, J=8 Hz, 1H). Mass spectral data: [M+H]$^+$ found, 212, calc, 212.

Scheme 9.

Alkylation Procedure:

1,3-di-1-triazolebenzene (0.5 g, 2.35 mmol), benzyl bromide (1.12 mL, 9.42 mmol), and acetonitrile (50 mL) were added to a round bottom flask. The solution was then refluxed at 110° C. for 16 hours. The reaction was then cooled to room temperature, and the volatiles were removed under vacuum. The crude product was washed with 20 mL of dichloromethane yielding 1.18 g of purified product. $^1$H NMR (DMSO) δ 11.32 (s, 2H), 9.67 (s, 2H), 8.52 (t, J=2 Hz, 1H), 8.21 (dd, J$^1$=2 Hz, J$^2$=8 Hz, 2H), 8.05 (dd, J$^1$=8 Hz, J$^2$=10 Hz, 1H), 7.65-7.40 (m, 10H), 5.65 (s, 4H). Mass spectral data: [M-2Br]$^+$ found, 394: calc, 394. Mass spectral data: [M-Br]$^+$ found, 473, 475; calc, 473,475.

Scheme 10.

Metallation/Transmetallation Procedure:

The bis-triazolium bromo salt (10 mg, 0.018 mmol), tetrakis(dimethylamido) zirconium (IV) (12 mg, 0.045 mmol), and dichloromethane (0.5 mL) were added to a sealable reaction vessel. The solution was stirred at room temperature for 2 hours. Dibromo(1,5-cyclooctadiene)platinum (II) (6.73 mg, 0.18 mmol) was then added and the solution was stirred for 24 hours. The solution was filtered through Celite and rinsed with an additional 3 mL of dichloromethane to extract residual product from the filter. The filtrate was then concentrated down under vacuum yielding 29 mg of crude product.

Scheme 11

In-air metalation procedure: The bis-triazolium bromo salt (10 mg, 0.018 mmol), dibromo(1,5-cyclooctadiene)platinum (II) (6.73 mg, 0.18 mmol), triethylamine (4.15 mg, 0.041 mmol), potassium bromide (6.42 mg, 0.054 mmol), and MeCN (0.5 mL) were added to sealable reaction vessel. The solution was heated at 80° C. for 16 hours. Following heating, the solution was filtered through a frit (fine grade), and the filtrate was concentrated down under vacuum yielding 13 mg of product.

Scheme 12

Mass spectral data: [M − Br + COD]⁺ found, 694, calc, 694.

The terms "comprising," "including," and "having," as used in the claims and specification herein, shall be considered as indicating an open group that may include other elements not specified. The terms "a," "an," and the singular forms of words shall be taken to include the plural form of the same words, such that the terms mean that one or more of something is provided. The term "one" or "single" may be used to indicate that one and only one of something is intended. Similarly, other specific integer values, such as "two," may be used when a specific number of things is intended. The terms "preferably," "preferred," "prefer," "optionally," "may," and similar terms are used to indicate that an item, condition or step being referred to is an optional (not required) feature of the invention.

The invention has been described with reference to various specific and preferred embodiments and techniques. However, it should be understood that many variations and modifications may be made while remaining within the spirit and scope of the invention. It will be apparent to one of ordinary skill in the art that methods, devices, device elements, materials, procedures and techniques other than those specifically described herein can be applied to the practice of the invention as broadly disclosed herein without resort to undue experimentation. All art-known functional equivalents of methods, devices, device elements, materials, procedures and techniques described herein are intended to be encompassed by this invention. Whenever a range is disclosed, all subranges and individual values are intended to be encompassed. This invention is not to be limited by the embodiments disclosed, including any shown in the drawings or exemplified in the specification, which are given by way of example and not of limitation.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

All references throughout this application, for example patent documents including issued or granted patents or equivalents, patent application publications, and non-patent literature documents or other source material, are hereby incorporated by reference herein in their entireties, as though individually incorporated by reference, to the extent each reference is at least partially not inconsistent with the disclosure in the present application (for example, a reference that is partially inconsistent is incorporated by reference except for the partially inconsistent portion of the reference).

REFERENCES (1) (a) Arduengo, A. J. *Acc. Chem. Res.* 1999, 32, 913-921; (b) Bourissou, D.; Guerret, O.; Gabbai, F. P.; Bertrand, G. *Chem. Rev.* 2000, 100, 39-91; (c) Schuster, O.; Yang, L.; Raubenheimer, H. G.; Albrecht, M. *Chem. Rev.* 2009, 109, 3445-3478.

(2) (a) Arduengo, A. J., III; Harlow, R. L.; Kline, M. *J. Am. Chem. Soc.* 1991, 113, 361-363; (b) Arduengo, A. J.; Dias, H. V. R.; Harlow, R. L.; Kline, M. *J. Am. Chem. Soc.* 1992, 114, 5530-5534.

(3) (a) Samojłowicz, C.; Bieniek, M.; Grela, K. *Chem. Rev.* 2009, 109, 3708-3742; (b) Díez-González, S.; Marion, N.; Nolan, S. P. *Chem. Rev.* 2009, 109, 3612-3676.

(4) (a) Mizuhata, Y.; Sasamori, T.; Tokitoh, N. *Chem. Rev.* 2009, 109, 3479-3511; (b) Hindi, K. M.; Panzner, M. J.; Tessier, C. A.; Cannon, C. L.; Youngs, W. J. *Chem. Rev.* 2009, 109, 3859-3884; (c) Arnold, P. L.; Casely, I. J. *Chem. Rev.* 2009, 109, 3599-3611.

(5) *The Chemistry of Pincer Compounds*; Morales-Morales, D.; Jensen, C. M., Eds.; Elsevier: New York, 2007.

(6) (a) Peris, E.; Crabtree Robert, H. In *The Chemistry of Pincer Compounds*; Morales-Morales, D., Jensen, C. M., Eds.; Elsevier: New York, 2007, p 107-124; (b) Poyatos, M.; Mata, J. A.; Peris, E. *Chem. Rev.* 2009, 109, 3677-3707.

(7) (a) Hahn, F. E.; Jahnke, M. C.; Pape, T. *Organometallics* 2007, 26, 150-154; (b) Danopoulos, A. A.; Tulloch, A. A. D.; Winston, S.; Eastham, G.; Hursthouse, M. B. *Dalton Trans.* 2003, 1009-1015.

(8) (a) Cho, J.; Hollis, T. K.; Helgert, T. R.; Valente, E. J. *Chem. Commun.* 2008, 5001-5003; (b) Bauer, E. B.; Andavan, G. T. S.; Hollis, T. K.; Rubio, R. J.; Cho, J.; Kuchenbeiser, G. R.; Helgert, T. R.; Letko, C. S.; Tham, F. S. *Org. Lett.* 2008, 10, 1175-1178; (c) Rubio, R. J.; Andavan, G. T. S.; Bauer, E. B.; Hollis, T. K.; Cho, J.; Tham, F. S.; Donnadieu, B. *J. Organomet. Chem.* 2005, 690, 5353-5364.

(9) (a) Pugh, D.; Boyle, A.; Danopoulos, A. A. *Dalton Trans.* 2008, 1087-1094; (b) Danopoulos, A. A.; Pugh, D.; Wright, J. A. *Angew. Chem. Int. Ed.* 2008, 47, 9765-9767.

(10) Hahn, F. E.; Jahnke, M. C.; Gomez-Benitez, V.; Morales-Morales, D.; Pape, T. *Organometallics* 2005, 24, 6458-6463.

(11) Raynal, M.; Pattacini, R.; Cazin, C. S. J.; Vallee, C.; Olivier-Bourbigou, H.; Braunstein, P. *Organometallics* 2009, 28, 4028-4047.

(12) Chakraborty, S.; Wadas, T. J.; Hester, H.; Schmehl, R.; Eisenberg, R. *Inorg. Chem.* 2005, 44, 6865-6878.

(13) Jarosz, P.; Du, P. W.; Schneider, J.; Lee, S. H.; McCamant, D.; Eisenberg, R. *Inorg. Chem.* 2009, 48, 9653-9663.

(14) Mayo, E. I.; Kilsa, K.; Tirrell, T.; Djurovich, P. I.; Tamayo, A.; Thompson, M. E.; Lewis, N. S.; Gray, H. B. *Photochem. Photobiol. Sci.* 2006, 5, 871-873.

(15) (a) Bauer, R.; Finkenzeller, W. J.; Bogner, U.; Thompson, M. E.; Yersin, H. *Org. Electron.* 2008, 9, 641-648; (b) Finkenzeller, W. J.; Hofbeck, T.; Thompson, M. E.; Yersin, H. *Inorg. Chem.* 2007, 46, 5076-5083; (c) Finkenzeller, W. J.; Thompson, M. E.; Yersin, H. *Chem. Phys. Lett.* 2007, 444, 273-279.

(16) (a) Moudam, O.; Rowan, B. C.; Alamiry, M.; Richardson, P.; Richards, B. S.; Jones, A. C.; Robertson, N. *Chem.*

*Commun.* 2009, 6649-6651; (b) Au, V. K.-M.; Wong, K. M.-C.; Zhu, N.; Yam, V. W.-W. *J. Am. Chem. Soc.* 2009, 131, 9076-9085; (c) Tam, A. Y.-Y.; Wong, K. M.-C.; Yam, V. W.-W. *J. Am. Chem. Soc.* 2009, 131, 6253-6260.

(17) Vargas, V. C.; Rubio, R. J.; Hollis, T. K.; Salcido, M. E. *Org. Lett.* 2003, 5, 4847-4849.

(18) Spencer, L. P.; Winston, S.; Fryzuk, M. D. *Organometallics* 2004, 23, 3372-3374.

(19) (a) Ahrens, S.; Strassner, T. *Inorg. Chim. Acta* 2006, 359, 4789-4796; (b) Berthon-Gelloz, G.; Buisine, O.; Briere, J. F.; Michaud, G.; Sterin, S.; Mignani, G.; Tinant, B.; Declercq, J. P.; Chapon, D.; Marko, I. E. *J. Organomet. Chem.* 2005, 690, 6156-6168.

(20) (a) Hoogervorst, W. J.; Koster, A. L.; Lutz, M.; Spek, A. L.; Elsevier, C. J. *Organometallics* 2004, 23, 1161-1164; (b) Zucca, A.; Doppiu, A.; Cinellu, M. A.; Stoccoro, S.; Minghetti, G.; Manassero, M. *Organometallics* 2002, 21, 783-785.

(21) (a) Vanderploeg, A.; Vankoten, G.; Vrieze, K.; Spek, A. L. *Inorg. Chem.* 1982, 21, 2014-2026; (b) Fantasia, S.; Petersen, J. L.; Jacobsen, H.; Cavallo, L.; Nolan, S. P. *Organometallics* 2007, 26, 5880-5889; (c) Grundemann, S.; Albrecht, M.; Loch, J. A.; Faller, J. W.; Crabtree, R. H. *Organometallics* 2001, 20, 5485-5488; (d) Peris, E.; Loch, J. A.; Mata, J.; Crabtree, R. H. *Chem. Commun.* 2001, 201-202.

(22) (a) Bohm, M. C.; Gleiter, R. *Angew. Chem.-Int. Edit. Engl.* 1983, 22, 329-330; (b) S. K. Lower, M. A. E.-S. *Chem. Rev.* 1966, 66, 199-241.

(23) (a) Zhang, L. Y.; Li, B.; Shi, L. F.; Li, W. L. *Opt. Mater.* 2009, 31, 905-911; (b) Evans, R. C.; Douglas, P.; Winscom, C. J. *Coord. Chem. Rev.* 2006, 250, 2093-2126.

(24) (a) Hung, L. S.; Chen, C. H. *Mater. Sci. Eng., R.* 2002, 39, 143-222; (b) Bulovi, V.; Burrows, P. E.; Forrest, S. R. In *Semiconductors and Semimetals*; Gerd, M., Ed.; Elsevier: New York, 1999; Vol. 64, p 255-306; (c) *Organic Light-Emitting Devices*; Shinar, J., Ed.; Springer: New York, 2004.

(25) Au, V. K. M.; Wong, K. M. C.; Zhu, N.Y.; Yam, V. W. W. *J. Am. Chem. Soc.* 2009, 131, 9076-9085.

REFERENCE SET TWO (RELATED TO NICKEL PINCER COMPLEXES)

1. Igau, A.; Grutzmacher, H.; Baceiredo, A.; Bertrand, G. *J. Am. Chem. Soc.* 1988, 110, (19), 6463-6466.
2. Arduengo, A. J.; Harlow, R. L.; Kline, M. *J. Am. Chem. Soc.* 1991, 113, (1), 361-363.
3. Arduengo, A. J. *Acc. Chem. Res.* 1999, 32, (11), 913-921.
4. Herrmann, W. A. *Angewandte Chemie-International Edition* 2002, 41, (8), 1290-1309.
5. Diez-Gonzalez, S.; Marion, N.; Nolan, S. P. *Chem. Rev.* 2009, 109, (8), 3612-3676.
6. Bohm, V. P. W.; Weskamp, T.; Gstottmayr, C. W. K.; Herrmann, W. A. *Angew. Chem. Int. Ed. Engl.* 2000, 39, (9), 1602-+.
7. Huynh, H. V.; Jothibasu, R. *Eur. J. Inorg. Chem.* 2009, (13), 1926-1931.
8. Schneider, S. K.; Rentzsch, C. F.; Krueger, A.; Raubenheimer, H. G.; Herrmann, W. A. *J. Mol. Catal. A—Chem.* 2007, 265, (1-2), 50-58.
9. Schaub, T.; Radius, U. *Chem. Eur. J.* 2005, 11, (17), 5024-5030.
10. Schaub, T.; Backes, M.; Radius, U. *Organometallics* 2006, 25, (17), 4196-4206.
11. Huynh, H. V.; Wong, L. R.; Ng, P. S. *Organometallics* 2008, 27, (10), 2231-2237.
12. Amii, H.; Uneyama, K. *Chem. Rev.* 2009, 109, (5), 2119-2183.
13. Meier, G.; Braun, T. *Angew. Chem. Int. Ed. Engl.* 2009, 48, (9), 1546-1548.
14. Torrens, H. *Coord. Chem. Rev.* 2005, 249, (17-18), 1957-1985.
15. Schaub, T.; Backes, M.; Radius, U. *J. Am. Chem. Soc.* 2006, 128, (50), 15964-15965.
16. Albrecht, M.; van Koten, G. *Angew. Chem. Int. Ed. Engl.* 2001, 40, (20), 3750-3781.
17. Benito-Garagorri, D.; Kirchner, K. *Acc. Chem. Res.* 2008, 41, (2), 201-213.
18. Singleton, J. T. *Tetrahedron* 2003, 59, (11), 1837-1857.
19. Pugh, D.; Boyle, A.; Danopoulos, A. A. *Dalton Trans.* 2008, (8), 1087-1094.
20. Danopoulos, A. A.; Tulloch, A. A. D.; Winston, S.; Eastham, G.; Hursthouse, M. B. *Dalton Trans.* 2003, (5), 1009-1015.
21. Tulloch, A. A. D.; Danopoulos, A. A.; Tizzard, G. J.; Coles, S. J.; Hursthouse, M. B.; Hay-Motherwell, R. S.; Motherwell, W. B. *Chem. Commun.* 2001, (14), 1270-1271.
22. Rubio, R. J.; Andavan, G. T. S.; Bauer, E. B.; Hollis, T. K.; Cho, J.; Tham, F. S.; Donnadieu, B. *J. Organomet. Chem.* 2005, 690, (23), 5353-5364.
23. Bauer, E. B.; Andavan, G. T. S.; Hollis, T. K.; Rubio, R. J.; Cho, J.; Kuchenbeiser, G. R.; Helgert, T. R.; Letko, C. S.; Tham, F. S. *Org. Lett.* 2008, 10, (6), 1175-1178.
24. Cho, J.; Hollis, T. K.; Helgert, T. R.; Valente, E. J. *Chem. Commun.* 2008, (40), 5001-5003.
25. Spencer, L. P.; Winston, S.; Fryzuk, M. D. *Organometallics* 2004, 23, (14), 3372-3374.
26. Shukla, P.; Johnson, J. A.; Vidovic, D.; Cowley, A. H.; Abernethy, C. D. *Chem. Commun.* 2004, (4), 360-361.
27. van der Vlugt, J. I.; Lutz, M.; Pidko, E. A.; Vogt, D.; Spek, A. L. *Dalton Trans.* 2009, (6), 1016-1023.
28. Pandarus, V.; Zargarian, D. *Organometallics* 2007, 26, (17), 4321-4334.
29. Gomez-Benitez, V.; Baldovino-Pantaleon, O.; Herrera-Alvarez, C.; Toscano, R. A.; Morales-Morales, D. *Tetrahedron Lett.* 2006, 47, (29), 5059-5062.
30. Boro, B. J.; Dickie, D. A.; Goldberg, K. I.; Kemp, R. A. *Acta Crystallogr.* 2008, E64, M1304-U759.
31. Kuroda, J. I.; Inamoto, K.; Hiroya, K.; Doi, T. *Eur. J. Org. Chem.* 2009, (14), 2251-2261.
32. Liu, A. L.; Zhang, X. M.; Chen, W. Z. *Organometallics* 2009, 28, (16), 4868-4871.

REFERENCES RELATED TO BIA (1) (a) Clavier, H.; Nolan, S. P. *Chem. Commun.* 2010, 46, 841-861; (b) Jacobsen, H.; Correa, A.; Poater, A.; Costabile, C.; Cavallo, L. *Coord. Chem. Rev.* 2009, 253, 687-703; (c) Liddle, S. T.; Edworthy, I. S.; Arnold, P. L. *Chem. Soc. Rev.* 2007, 36, 1732-1744; (d) Arduengo, A. J. *Acc. Chem. Res.* 1999, 32, 913-921; (e) Bourissou, D.; Guerret, O.; Gabbai, F. P.; Bertrand, G. *Chem. Rev.* 2000, 100, 39-91; (f) Schuster, O.; Yang, L.; Raubenheimer, H. G.; Albrecht, M. *Chem. Rev.* 2009, 109, 3445-3478; (g) Diez-Gonzalez, S.; Marion, N.; Nolan, S. P. *Chem Rev* 2009, 109, 3612-3676; (h) Poyatos, M.; Mata, J. A.; Peris, E. *Chem Rev* 2009, 109, 3677-3707; (i) Hahn, F. E.; Jahnke, M. C. *Angew. Chem.-Int. Edit.* 2008, 47, 3122-3172.

(2) (a) Cho, J.; Hollis, T. K.; Helgert, T. R.; Valente, E. J. *Chem. Commun.* 2008, 5001-5003; (b) Bauer, E. B.; Andavan, G. T. S.; Hollis, T. K.; Rubio, R. J.; Cho, J.; Kuchenbeiser, G. R.; Helgert, T. R.; Letko, C. S.; Tham, F. S. *Org.*

*Lett.* 2008, 10, 1175-1178; (c) Rubio, R. J.; Andavan, G. T. S.; Bauer, E. B.; Hollis, T. K.; Cho, J.; Tham, F. S.; Donnadieu, B. *J. Organomet. Chem.* 2005, 690, 5353-5364; (d) Chianese, A. R.; Mo, A.; Lampland, N. L.; Swartz, R. L.; Bremer, P. T. *Organometallics* 2010, 29, 3019-3026.

(3) (a) Danopoulos, A. A.; Tulloch, A. A. D.; Winston, S.; Eastham, G.; Hursthouse, M. B. *Dalton Trans.* 2003, 1009-1015; (b) Hahn, F. E.; Jahnke, M. C.; Pape, T. *Organometallics* 2007, 26, 150-154.

(4) (a) Danopoulos, A. A.; Pugh, D.; Wright, J. A. *Angew. Chem. Int. Ed.* 2008, 47, 9765-9767; (b) Pugh, D.; Boyle, A.; Danopoulos, A. A. *Dalton Trans.* 2008, 1087-1094.

(5) Hahn, F. E.; Jahnke, M. C.; Gomez-Benitez, V.; Morales-Morales, D.; Pape, T. *Organometallics* 2005, 24, 6458-6463.

(6) (a) Moser, M.; Wucher, B.; Kunz, D.; Rominger, F. *Organometallics* 2007, 26, 1024-1030; (b) Wucher, B.; Moser, M.; Schumacher, S. A.; Rominger, F.; Kunz, D. *Angew. Chem.-Int. Edit.* 2009, 48, 4417-4421.

(7) Perez-Trujillo, M.; Maestre, I.; Jaime, C.; Alvarez-Larena, A.; Piniella, J. F.; Virgili, A. *Tetrahedron-Asymmetr* 2005, 16, 3084-3093.

REFERENCES RELATED TO ABNORMAL CARBENES (1) Igau, A.; Grutzmacher, H.; Baceiredo, A.; Bertrand, G. *Journal of the American Chemical Society* 1988, 110, 6463.

(2) Arduengo, A. J.; Harlow, R. L.; Kline, M. *Journal of the American Chemical Society* 1991, 113, 361.

(3) Crudden, C. M.; Allen, D. P. *Coordination Chemistry Reviews* 2004, 248, 2247.

(4) Jacobsen, H.; Correa, A.; Poater, A.; Costabile, C.; Cavallo, L. *Coordination Chemistry Reviews* 2009, 253, 687.

(5) Liddle, S. T.; Edworthy, I. S.; Arnold, P. L. *Chemical Society Reviews* 2007, 36, 1732.

(6) Scott, N. M.; Nolan, S. P. *European Journal of Inorganic Chemistry* 2005, 1815.

(7) Peris, E.; Crabtree, R. H. *Coordination Chemistry Reviews* 2004, 248, 2239.

(8) Herrmann, W. A. *Angewandte Chemie-International Edition* 2002, 41, 1290.

(9) Hillier, A. C.; Grasa, G. A.; Viciu, M. S.; Lee, H. M.; Yang, C. L.; Nolan, S. P. *Journal of Organometallic Chemistry* 2002, 653, 69.

(10) Marion, N.; Nolan, S. P. *Chemical Society Reviews* 2008, 37, 1776.

(11) Arnold, P. L.; Pearson, S. *Coordination Chemistry Reviews* 2007, 251, 596.

(12) John, A.; Shaikh, M. M.; Ghosh, P. *Dalton Trans* 2009, 10581.

(13) Tang, C. Y.; Smith, W.; Vidovic, D.; Thompson, A. L.; Chaplin, A. B.; Aldridge, S. *Organometallics* 2009, 28, 3059.

(14) Crittall, M. R.; Ellul, C. E.; Mahon, M. F.; Saker, O.; Whittlesey, M. K. *Dalton Transactions* 2008, 4209.

(15) Appelhans, L. N.; Incarvito, C. D.; Crabtree, R. H. *Journal of Organometallic Chemistry* 2008, 693, 2761.

(16) Eguillor, B.; Esteruelas, M. A.; Olivan, M.; Puerta, M. *Organometallics* 2008, 27, 445.

(17) Grundemann, S.; Kovacevic, A.; Albrecht, M.; Faller, J. W.; Crabtree, R. H. *Chemical Communications* 2001, 2274.

(18) Grundemann, S.; Kovacevic, A.; Albrecht, M.; Faller, J. W.; Crabtree, R. H. *Journal of the American Chemical Society* 2002, 124, 10473.

(19) Stylianides, N.; Danopoulos, A. A.; Tsoureas, N. *Journal of Organometallic Chemistry* 2005, 690, 5948.

(20) Song, G. Y.; Wang, X. J.; Li, Y. X.; Li, X. W. *Organometallics* 2008, 27, 1187.

(21) Song, G. Y.; Li, X. W.; Song, Z. C.; Zhao, J.; Zhang, H. J. *Chemistry—a European Journal* 2009, 15, 5535.

(22) Baya, M.; Eguillor, B.; Esteruelas, M. A.; Olivan, M.; Onate, E. *Organometallics* 2007, 26, 6556.

(23) Heckenroth, M.; Neels, A.; Garnier, M. G.; Aebi, P.; Ehlers, A. W.; Albrecht, M. *Chemistry—a European Journal* 2009, 15, 9375.

(24) Heckenroth, M.; Kluser, E.; Neels, A.; Albrecht, M. *Dalton Trans* 2008, 6242.

(25) Rubio, R. J.; Andavan, G. T. S.; Bauer, E. B.; Hollis, T. K.; Cho, J.; Tham, F. S.; Donnadieu, B. *Journal of Organometallic Chemistry* 2005, 690, 5353.

(26) Vargas, V. C.; Rubio, R. J.; Hollis, T. K.; Salcido, M. E. *Organic Letters* 2003, 5, 4847.

(27) So, Y. H. *Macromolecules* 1992, 25, 516.

We claim:

1. A compound having the formula:

wherein R is an alkyl or aryl group that may contain heteroatoms;

$R^1$ is a hydrogen, alkyl or aryl group that may contain a heteroatom substituent;

$R^2$, $R^3$, $R^4$, $R^5$ are selected from the group consisting of hydrogen, alkyl or aryl groups that may contain heteroatoms;

M is selected from the group consisting of metals;

L is a ligand;

x is any number between 0 and 3;

and n is any number between 0 and 6.

2. The compound of claim 1, wherein at least one of R, $R^1$, $R^2$, $R^3$, $R^4$, or $R^5$ comprises at least one heteroatom, and wherein said at least one heteroatom comprises at least one silicon atom.

3. The compound of claim 1, wherein M is platinum.

4. The compound of claim 1, wherein M is palladium.

5. The compound of claim 1, wherein M is nickel.

6. The compound of claim 1 wherein M is selected from the group consisting of ruthenium, iron, rhodium, iridium, titanium, osmium, cobalt, gold, silver, and copper.

7. A method of preparing the compound of claim 1 comprising the steps of:

a) combining a bis-salt and a metal amido reagent in an organic solvent;

b) after a period of time adding a second metal salt to effect transmetallation; and c) Adding water to form a precipitate.

8. The method of claim 7 wherein the metal of the metal amido reagent is selected from the list consisting of Zirconium, Titanium, Hafnium, Tantalum, and Scandium.

9. A method for producing light of wavelength in range of 360 nm to 1300 nm comprising the steps of:
   a) placing the compound of claim 1 on a surface or in a film; and
   b) irradiating said compound with UV light or other excitation energy sources.

10. A method for producing light of wavelength in range of 360 nm to 1300 nm comprising the steps of:
   a) placing the compound of claim 1 in a matrix; and
   b) irradiating the compound with UV light or other excitation energy sources.

11. A method of producing light wherein the compound of claim 1 is excited by an energy source.

12. A device incorporating the compound of claim 1.

13. A method for making a laser wherein the compound of claim 1 is excited by an energy source.

14. A device for producing light comprising the compound of claim 1.

15. The device of claim 14 wherein said light is white light.

16. The device of claim 14 wherein said light is laser.

17. The device of claim 14 wherein said compound is excited as part of a method for making an OLED.

18. The compound of claim 1 wherein said compound is excited by an energy source as part of a photovoltaic cell.

19. An electroluminescent device utilizing the compound of claim 1.

20. A device using the compound of claim 1 wherein the compound is phosphorescent.

21. A compound having the formula wherein R, R2 are selected from the group consisting of a hydrogen, alkyl or aryl group that may contain heteroatoms;

$R^1$ is an alkyl or aryl group that may contain heteroatoms;
R3 is selected from the group consisting of hydrogen, alkyl or aryl groups that may contain heteroatoms;
M is selected from the group consisting of metals;
L is a ligand;
x is any number between 0 and 3;
and n is any number between 0 and 6.

22. A method of preparing the compound of claim 21 comprising the steps of:
   a) combining a bis-salt and a metal amido reagent in an organic solvent;
   b) after a period of time adding a second metal salt to effect transmetallation; and
   c) Adding water to form a precipitate.

23. The method of claim 22 wherein the metal of the metal amido reagent is selected from the list consisting of Zirconium, Titanium, Hafnium, Tantalum, and Scandium.

24. A method for producing light of wavelength in range of 360 nm to 1300 nm comprising the steps of:
   a) placing the compound of claim 21 on a surface or in a film; and
   b) irradiating said compound with UV light or other excitation energy sources.

25. A method of producing light wherein the compound of claim 21 is excited by an energy source.

26. A device incorporating the compound of claim 21.

27. A method for making a laser wherein the compound of claim 21 is excited by an energy source.

28. A device for producing light comprising the compound of claim 21.

29. The device of claim 28 wherein said light is white light.

30. The device of claim 28 wherein said light is laser.

31. The device of claim 30 wherein said compound is excited as part of a method for making an OLED.

32. The compound of claim 21 wherein said compound is excited by an energy source as part of a photovoltaic cell.

33. An electroluminescent device utilizing the compound of claim 21.

34. A device using the compound of claim 21 wherein the compound is phosphorescent.

* * * * *